United States Patent
Accoto et al.

(10) Patent No.: US 9,131,833 B2
(45) Date of Patent: Sep. 15, 2015

(54) LOCOMOTION DEVICE FOR ENDOSCOPIC APPLICATIONS AND RELATED METHODS

(75) Inventors: Dino Accoto, Andrano (IT); Serena Passanisi, Caltanissetta (IT)

(73) Assignee: UNIVERSITA CAMPUS BIO-MEDICO DI ROMA, Rome (IT)

( * ) Notice: Subject to any disclaimer, the term of this patent is extended or adjusted under 35 U.S.C. 154(b) by 0 days.

(21) Appl. No.: 13/484,057

(22) Filed: May 30, 2012

(65) Prior Publication Data
US 2013/0324796 A1 Dec. 5, 2013

(51) Int. Cl.
*A61B 1/00* (2006.01)
*A61B 1/04* (2006.01)
*A61M 31/00* (2006.01)
*A61M 25/00* (2006.01)

(52) U.S. Cl.
CPC ........... *A61B 1/00156* (2013.01); *A61B 1/0016* (2013.01); *A61B 1/041* (2013.01)

(58) Field of Classification Search
USPC ......... 600/101, 104, 106, 114, 115, 127, 129, 600/146–152; 604/95.01–95.05, 264, 271; 606/1; 356/241.1, 241.3–241.6
See application file for complete search history.

(56) References Cited

U.S. PATENT DOCUMENTS

| | | |
|---|---|---|
| 2002/0156347 A1 | 10/2002 | Kim et al. |
| 2004/0204702 A1 | 10/2004 | Ziegler et al. |
| 2005/0154278 A1 | 7/2005 | Cabiri et al. |
| 2006/0070775 A1 | 4/2006 | Anhalt et al. |
| 2010/0198011 A1* | 8/2010 | Ziegler et al. ................. 600/114 |
| 2012/0029283 A1* | 2/2012 | Yamakawa et al. ........... 600/114 |
| 2012/0238804 A1* | 9/2012 | Yamakawa et al. ........... 600/101 |

FOREIGN PATENT DOCUMENTS

IT RM2009A000635 6/2011

OTHER PUBLICATIONS

English translation of Italian Application No. RM2009A0000635 including statement concerning accuracy of the translation.
Italian Search Report completed on Jul. 15, 2010 for Italian Application No. RM2009A0000635 in the name of Universita Campus Bio-Medico Di Roma.
Italian Written Opinion completed on Jul. 15, 2010 for Italian Application No. RM2009A0000635 in the name of Universita Campus Bio-Medico Di Roma.

* cited by examiner

Primary Examiner — Ryan Henderson
(74) Attorney, Agent, or Firm — Steinfl & Bruno LLP

(57) ABSTRACT

A locomotion device and related methods for navigation into an intracorporeal cavity such as a gastrointestinal tract are described. The locomotion device is based upon rotating pinching organs, associated actuators, and transmission systems wherein the rotating pinching organs are placed side by side and rotate in an opposite direction in order to draw and retain a tissue portion and establish an anchoring point of the locomotion device onto the substratum.

12 Claims, 3 Drawing Sheets

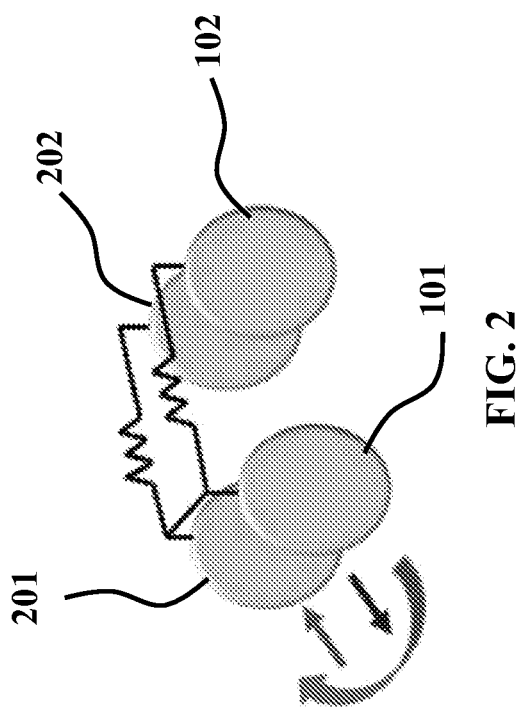
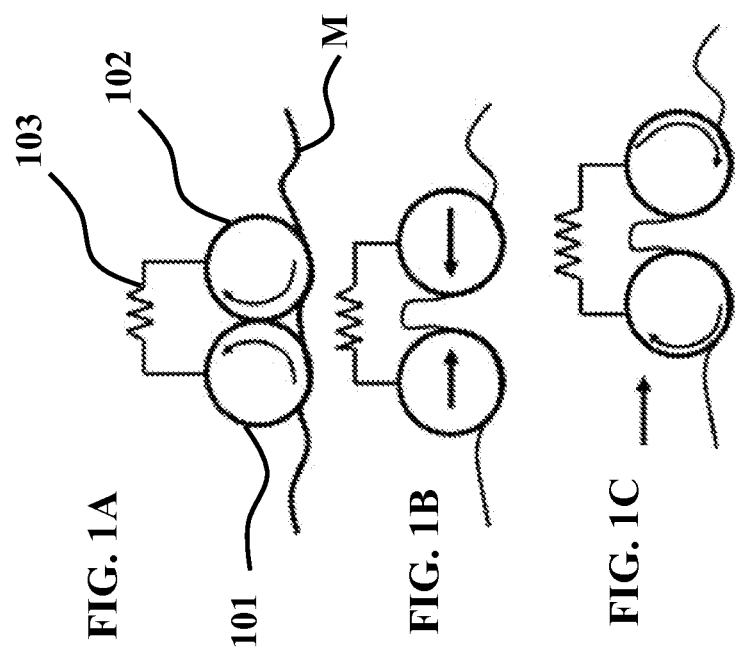

LOCOMOTION DEVICE FOR ENDOSCOPIC APPLICATIONS AND RELATED METHODS

CROSS-REFERENCE TO RELATED APPLICATION

The present application is related to Italian Patent Application No. RM2009A000635 filed on Dec. 2, 2009, and open to public inspection as of Jun. 3, 2011, which is herein incorporated by reference in its entirety.

FIELD

The present disclosure relates to a locomotion device and method, particularly suitable for endoscopic applications, especially in the field of digestive endoscopy.

SUMMARY

According to a first aspect of the disclosure, a locomotion device is described. The device comprises pinching means, configured to draw and retain a substratum portion to establish an anchoring point of the locomotion device onto the substratum, wherein the pinching means comprises a pair of rotating elements capable of being driven according to reciprocally-opposite rotation directions and capable of performing the drawing and retaining function by means of the reciprocally-opposite rotation, wherein the overall arrangement is such that the locomotion device is capable of moving onto a deformable substratum and configured for endoscopic navigation into a gastro-intestinal tract.

According to a second aspect of the disclosure, a method for performing locomotion of a locomotion device onto a deformable substratum is provided. The method comprises: performing a pinching, comprising drawing and retaining a viscoelastic substratum portion between pinching means of the device to establish an anchoring point of the device onto the substratum; and performing a moving step, subsequent to the pinching step, comprising moving the device forward with respect to the substratum, gradually releasing the substratum drawn in the pinching step.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 1A, 1B and 1C show an operation scheme of a locomotive device according the present disclosure, each one with reference to a respective pinch or moving forward step.

FIG. 2 shows an operation scheme of an alternative embodiment of the device of FIG. 1.

DETAILED DESCRIPTION

Figure 3:
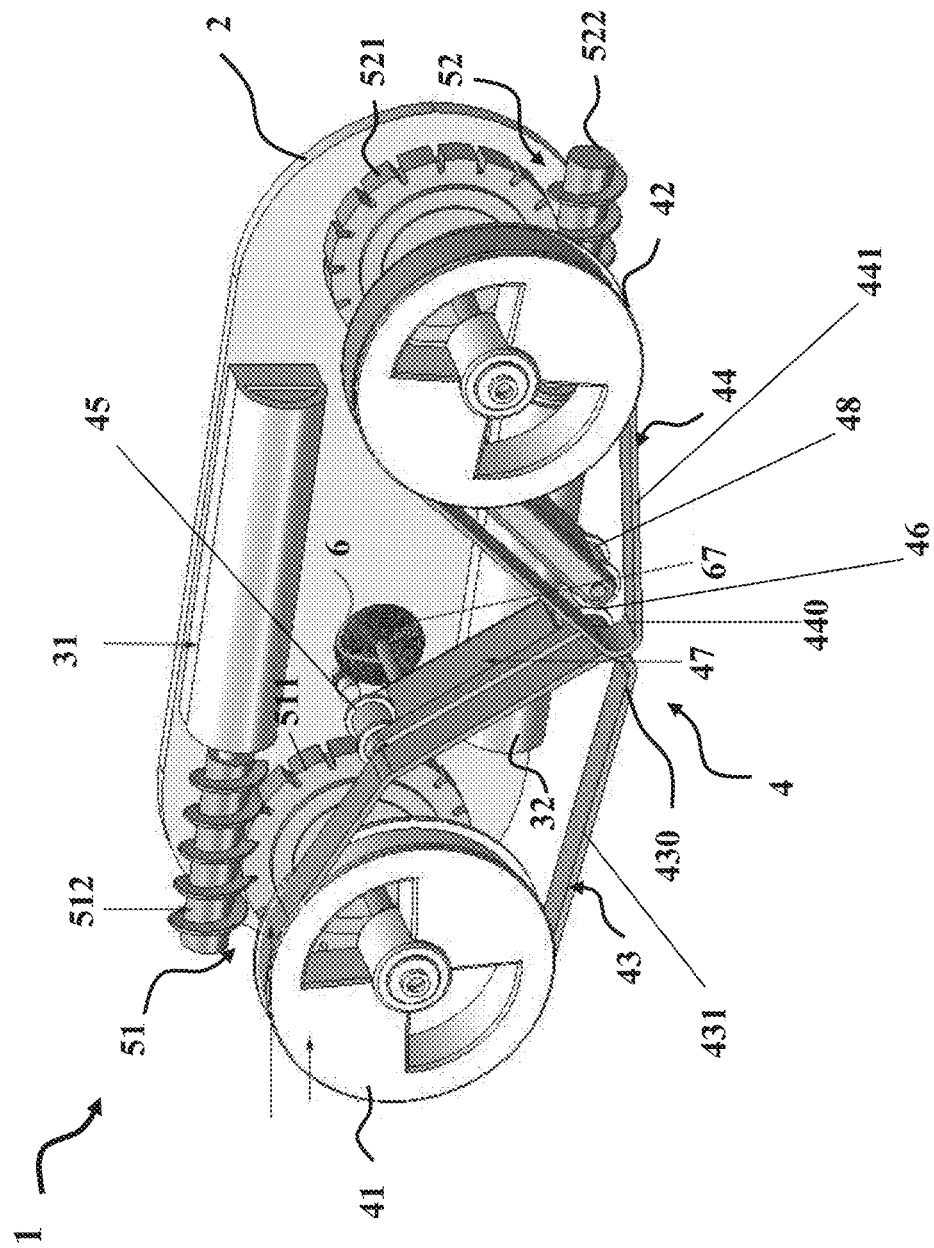
FIG. 3 refers to a preferred embodiment of the device of FIG. 1, showing an exploded view thereof.

Endoscopic procedures can require the use of a probe, which is inserted through natural body orifices and which is typically provided with sensors, displaying means and sometimes bioptic instruments.

Endoscopic procedures can also require a good manual ability of an endoscopist performing the insertion and managing probe navigation.

In case of interventions upon a gastrointestinal tract, the procedures can cause psychological and physical discomfort for a patient, thus leading development of robotic endoscopes capable of self-propulsion and an improved skill of an instrument during locomotion.

Existing proposals for locomotion techniques of endoscopic devices can be subdivided in two families, a first family being cabled systems and a second family being robotic capsules. With respect to the first family, a first approach to locomotion is the so-called "inchworm-like" approach, which simulates worms' moving.

In particular, in this approach the device moves by alternating extension and contraction steps of a suitable extensible body, thus providing a peristaltic movement. This approach can also require two gripping members arranged at device extremities, in to transfer the forces necessary for locomotion to the substratum.

A second approach of the first family is a "snake-like" approach, wherein an undulatory movement of a central structure is generated, for example, by means of shape memory alloys positioned around the central structure, in such a manner that the robot can orient and fold in a tridimensional manner.

Concerning the second family, comprising locomotion techniques for robotic capsules, a first known approach provides for a passive motion, based upon peristaltic waves of an intestinal tract to be explored.

Recently, a robotic capsule equipped with a locomotion system based upon legs made of shape memory alloy threads, which can provide great elasticity to moving organs, was developed. This capsule is capable of being stopped at a certain location by means of small hooks placed at terminal parts of the legs, but it is not capable of rotating on the spot and therefore of orienting itself with respect to certain target. Moreover, such locomotion system occupies almost a whole capsule inner space, making it difficult to house batteries, display systems and other tools.

A third approach for robotic capsules provides for a locomotion system based upon use of magnetic fields. In particular, by varying an external magnetic field, it is possible to control the capsule's position and orientation by means of suitable magnets integrated in the capsule.

The locomotion systems mentioned above can have some drawbacks, in particular that: they can lead to a difficulty in maintaining a grip with respect to an explored region of a body and consequently can affect an ability to maintain a position when external disturbing actions occur, such as peristaltic waves; they can lack ability to rotate on the spot and/or to orient during locomotion, or can lead to encumbering or mechanically complex systems to obtain such orientation; in some cases and also in view of the above-mentioned potential drawbacks, the they can lead to mechanical complexity of the unit implementing locomotion; and they can lead to a need for apparatuses and tools to be arranged upon or around the patient, for example, magnetic jackets and/or robotic manipulators, for device localization and driving by suitable magnetic fields arranged externally to the patient's body.

The above considerations have been described with reference to the field of navigation into a region of a body, and particularly into a gastro-intestinal tract, however such considerations can be applicable in industrial contexts where there can be a need for navigating onto a deformable, for example soft, elastic or visco-elastic substratum, e.g. onto tissues, membranes, tubes or the like.

The present disclosure, allows in some embodiments a substantially constant and reliable gripping of the locomotion device onto soft and/or deformable (e.g. elastic or viscoelastic) substratum, and in particular onto the external mucous membrane of the hollow organs of the human body, for example the gastro intestinal tract. This is obtained by a locomotion system that can be realized in an easy mechanical manner, which is reliable and self-contained, not requiring specific external auxiliary tools.

Furthermore, the device according to the disclosure is suitable for a compact construction to reduce residual volume inside the robotic capsule or equivalent means housing the locomotion device.

In embodiments which provide two or more pairs elements in relative motion with respect to each other, the locomotion device of the disclosure is capable of varying its orientation and is thus capable of modifying the locomotion direction.

FIGS. 1A-C show a locomotion principle according to some embodiments.

The locomotion principle shown in FIG. 1, which can be referred to as "pinch locomotion", is based upon the possibility of performing micro-pinches onto the substratum, for example, onto an intestinal mucous membrane, utilizing suitable robot organs which can exert a gripping or ("pinching") force and a locomotion force onto the substratum, within safety limits of the substratum.

With reference to FIGS. 1A-1C, the pinch locomotion principle can be understood at an abstract level by considering two wheels, or rolling organs, 101 and 102 adjacent and tangential to a mucous membrane M. In some embodiments, rolling organs 101 and 102 are connected by an elastic element 103 that opposes a change in the distance between the two respective centers, and thus can act as a contrast element. The force exerted by the organ provides the necessary gripping, i.e. pinching, force. The elastic element can be implemented in a plurality of manners, i.e. by helicoidal springs or elastic blades. It can also be substituted by an active, i.e. actuated, organ, for example a screw—female screw system, having the same function of generating a pinching force.

In some embodiments locomotion takes place in two steps. During a first step ("pinching"), shown in FIGS. 1A and 1B, two wheels 101 and 102 rotate in opposite directions to draw a substratum. In this step the substratum M, e.g. a gastrointestinal mucous membrane, due at least in part to the softness thereof, can be drawn between the two rolling elements 101 and 102 by the tensile stress exerted by each element by virtues of the motion.

Still in this phase, elastic element 103 can enable a passive regulation of distance between the two wheels 101 and 102 and the distance can vary with the thickness of the substratum portion drawn by the rotation. The action exerted by contrast elastic element 103 can enable maintenance of the pinch onto the substratum.

In some embodiments, in a step sequent to pinching, for example, as shown in FIG. 1C, wheels 101 and 102 rotate in a same direction, permitting system translation. During translation, a front-moving organ draws a new substratum portion between the two rolling organs, while a posterior organ releases an equal quantity of substratum.

The system shown in FIGS. 1A-1C comprises one pair of rolling organs only, which can allow a mono-dimensional movement (e.g. front and rear), without any "on the spot" rotating capacity and any orienting capacity during locomotion.

To allow system orientation, a second pair of wheels 201 and 202 can be added, as shown in FIG. 2. In this configuration locomotion device rotation can be obtained similarly to that of systems which are provided with two autonomous tracks, namely by driving the two pairs of wheels at different speeds.

In some embodiments and with reference to FIG. 3, a locomotion device disclosure is globally denoted by 1. Device 1 can be used for navigation into a gastro-intestinal tract cavity.

Device 1 comprises a substantially flat frame or chassis 2, two driving units, 31 and 32 respectively, that are mounted onto the frame 2 at transversally-opposite parts of the frame, and pinching means, driven by driving unit 31 and 32 and denoted globally by 4.

The specific arrangement and construction of the components of Device 1 is described in greater detail below.

In the present example of Device 1, each driving unit 31, 32 comprises a respective motor, e.g. of an electromagnetic type, which, in some embodiments is associated with a respective redactor unit, for example, an epicycloidal type of redactor unit (not shown in the figures).

By way of example and not of limitation, each motor can be a commercial, brushless DC motor, having an external diameter lower than approximately 5 mm (for example, micro-motor Smoovy with an external diameter of approximately 1.9 mm and integrating an epicycloidal redactor unit with reduction ratio approximately 1:47).

In order to further reduce an outlet transmission ratio, further transmission means—globally denoted by 51 and 52—can be associated with each driving unit 31, 32. In the present example, such further transmission means are a coupling of ring gear 511, 521 with an endless screw 512, 522.

By way of example and not of limitation, the reduction ratio can be approximately 18:1, so that the global reduction ratio is approximately 1:846.

Wheel 511, 521 of each of the couplings 51, 52 is fixed with a respective first or second principal pulley 41, 42 of pinching means 4.

In some embodiments, pinching means further comprise, for each first or second principal pulley 41, 42, a respective first or second belt 43, 44, which engages the respective principal pulley 41, 42.

A first belt 43 can be rotated by first pulley 41 and tensioned by means of two further auxiliary follower pulleys 45, 46 which can be mounted at relative longitudinal ends of an equalizer 47.

The overall arrangement can be such that belt 43 has a substantially rounded trapezoidal profile during operation.

Equalizer 47 can be mounted in an oscillating manner onto frame 2 by means of a fixed pin 6, to enable a rotation of the equalizer 47 around an axis substantially orthogonal with respect to frame 2. A contrast elastic means can be interposed between pin 6 and equalizer 47. In some embodiments, the contrast elastic means is a torsion spring 67.

A second belt 44 can be rotated by the principal pulley 42 and tensioned by a further auxiliary follower pulley 48 which can be mounted at a longitudinal end of a support 49.

In some embodiments, the overall arrangement is such that the second belt 44 has a substantially rounded triangular profile during operation.

Moreover, in some embodiments, the overall arrangement is such that the two belts 43 and 44 face and are adjacent to each other at respective rounded angle (or arrow tip) portions 430, 440. In correspondence of the belt portions 430, 440 the action of pinching takes place, as described in detail later.

In some embodiments, adjacent to the belt portions—and upstream to the belt portions with respect to the rotation direction that provides the pinching, belts 43 and 44 can each have a rectilinearly developing portion, respectively 431 and 441, which remain substantially parallel to and in touch with the substratum during operation, thus exercising on the substratum a drawing action caused by friction.

Therefore, belts 43 and 44 can be made by a material and with a superficial geometry capable of establishing an effective friction for obtaining pinching and locomotion on the substratum, e.g., in case of biological tissues such as the mucous membrane of the gastrointestinal tract, by a material and with a superficial geometry capable of assuring biotribological conditions suitable for generating a sufficient friction/adhesion. By way of example and not of limitation, belts' surfaces can comprise micro-hooks with dimensions capable of avoiding intolerable lesions for a mucous membrane of the gastrointestinal tract. Operation modes of device 1 are now described.

In some embodiments, driving units 31 and 32, through transmission means 51 and 52, drive in rotation main pulleys 41 and 42, and therefore belts 43 and 44 associated therewith, according to an opposed rotation direction, as described above with reference to Figures 1A and 1B.

A substratum portion, for example an intestinal substratum, can then be drawn between facing portions 430, 440 of the belts 43, 44 so that a pinching action as described above can be obtained.

To permit the pinching action, the oscillating connection of equalizer 47 to frame 2 is such that belt portion 430 can depart from opposite belt portion 440 to enable an insertion of a substratum portion between them.

At the same time, the contrast action of spring 67 can allow for retention of the substratum. In particular, deformation of spring 67, which opposes elastically to the equalizer displacement, generates a force that is transmitted to the substratum by auxiliary pulley 46 and 48 and which assures grip maintenance in presence of external forces, e.g. pushes caused by peristaltic contractions.

In some embodiments, oscillating compensator 47, suitably dimensioned, enables maintaining of a first belt tension, independently from the thickness of a drawn substratum.

As would be understood by a skilled person the pinching function, and particularly the substratum drawing between the two facing portions 430 and 440, can be favored by the interaction between substratum and rectilinearly developing tracts 431 and 441 of belts 43 and 44.

In a subsequent step, belts 43 and 44 can be actuated according to the same direction of rotation, so as to cause locomotion according to the modes already described with reference to FIG. 1C.

In some embodiments, device 1 can be associated with or fixed to a control unit—or selective driving means—of pinching means 4, capable of controlling or managing the actuation of pinching means 4, for example, according to the steps sequence described in conjunction with FIGS. 1A, 1B and 1C.

Moreover, in some embodiments, corresponding to FIG. 2, the device can incorporate an additional pair of pulleys and corresponding, independent motor and transmission means, wherein the pairs of pulleys and associated driving components are arranged at opposite parts of the device so as to enable orientation variations of the latter.

As would also be understood by a skilled person, according to a further embodiment compatible with both the above-described embodiments, the elastic element or contrast spring can be absent. In these embodiments, substratum retaining can be controlled by the elastic deformability of the material of the pulleys or of alternative rotating elements performing the functions of the elastic element or contrast spring.

Figure 4A:
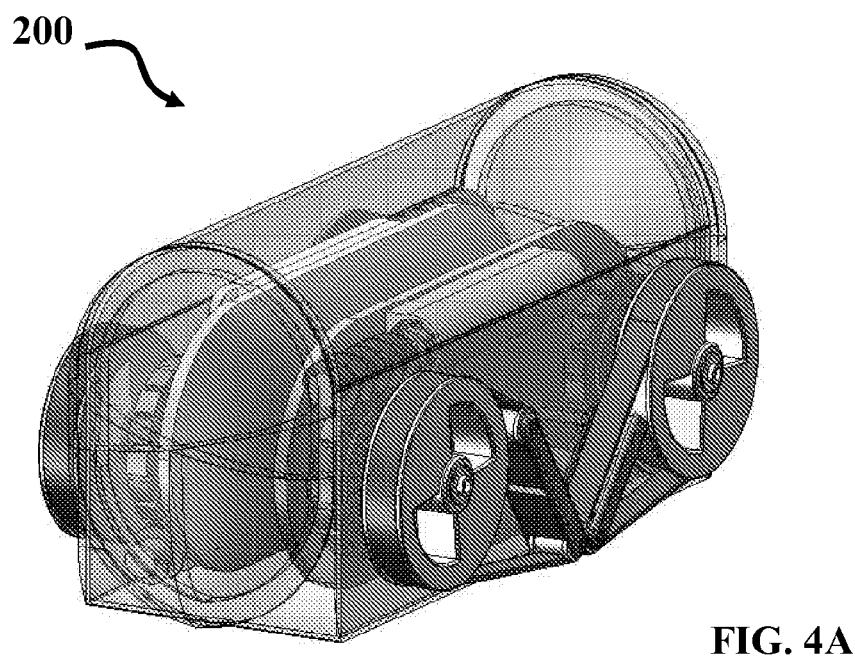
FIGS. 4A, 4B and 4C refer to an endoscopic capsule which incorporates device of FIG. 3, showing a lateral prospective view, a frontal view and a lateral view thereof, respectively.
Figure 4B:
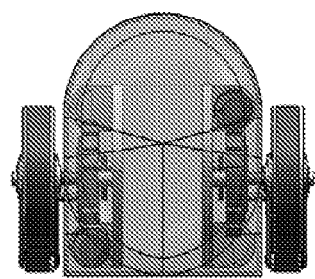
Figure 4C:
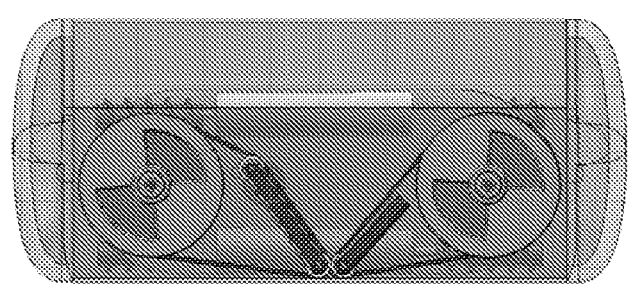

With reference to FIGS. 4A-4C, two devices such as the device described above with reference to FIG. 3 can be associated with an endoscopic capsule 200 and arranged symmetrically at the sides of the endoscopic capsule 200.

In some embodiments, an overall reduced encumbrance of the lateral locomotion devices can make large spaces available internally to the capsule to insert suitable instrumentation and supply systems, for example batteries or super capacitors. In particular, in some embodiments about 60% of the capsule inner space is available for housing instrumentation and/or supplies, including but not limited to batteries, displaying system, control system, and/or a telemetric system.

The device according to the present disclosure can allow in various embodiments the following a continuous maintenance of the grip upon an intestinal substratum which can in turn allow for obtaining a position control against possible external disturbing actions, such as peristaltic contractions; "on the spot" rotating capacity and therefore orientation capacity with respect to a target to be submitted to diagnostic or therapeutic attention; rotating capacity during locomotion in order to reach a target to be submitted to diagnostic or therapeutic attention; energetic efficacy: the power needed being compatible with that offered by commercial batteries presently on the market; compactness and providing possibility of high miniaturizing (length lower than approximately 30 mm and diameter lower than approximately 15 mm): an entire locomotion system capable of being mounted onto a robotic capsule having dimensions comparable with those of known passive robotic capsules; having almost 60% of the overall capsule volume free and usable for housing other sub-systems.

Finally, it would be understood by a skilled person that the disclosure also provides a locomotion method of a device on a soft substratum, for example a viscoelastic substratum, which in some embodiments comprises: a pinching step, in which a substratum portion is drawn and retained between pinching means which in some embodiments are the pinching means as described herein, so as to establish an anchoring point onto the substratum itself; and a moving step, subsequent to the pinching step, in which the device moves forward with respect to the substratum, gradually releasing the substratum drawn in the step.

The examples set forth above are provided to give those of ordinary skill in the art a complete disclosure and description of how to make and use the embodiments of the locomotion device for endoscopic applications and related methods of the disclosure, and are not intended to limit the scope of what the inventors regard as their disclosure. Modifications of the above-described modes for carrying out the disclosure can be used by persons of skill in the art, and are intended to be within the scope of the following claims.

Modifications of the above-described modes for carrying out the methods and devices herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the"

include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications can be made without departing from the spirit and scope of the present disclosure. Accordingly, other embodiments are within the scope of the following claims.

What is claimed is:

1. A locomotion device, comprising:
a pincher, configured to draw and retain a deformable substratum portion of a substratum of a mucous membrane of a hollow organ of a human body, which substratum is external to the locomotion device, to establish an anchoring point of the locomotion device onto the substratum, wherein the locomotion device is capable of being arranged externally to the substratum,
wherein the pincher comprises a pair of rotating elements capable of being driven according to reciprocally-opposite rotation directions and capable of drawing and retaining between them the substratum portion by a reciprocally-opposite rotation in said reciprocally-opposite rotation directions so as to perform a pinching and retaining step of the substratum,
wherein said rotating elements are also capable of being driven according to a same rotation direction so as to perform a translation step of the locomotion device onto the substratum,
wherein said rotating elements are formed of a pair of belts having respective facing portions provided with a relative rotation, the belts of said pair being configured to be in contact with the substratum and to draw and retain the substratum portion between them,
wherein a distance between the facing portions is variable to allow substratum pinching between the facing portions,
wherein the pincher comprises a contrast element configured to oppose a change in relative distance between the facing portions of said belts, said change being caused by a thickness of pinched tissue,
wherein the substratum portion is drawn in and pinched between said facing portions when driving the rotating elements in reciprocally-opposite rotation directions, wherein the substratum portion is maintained between the facing portions by a biasing force from the contrast element,
wherein the locomotion device alternates the pinching and retaining step of the substratum with the translation step onto the substratum,
and wherein the locomotion device is configured for endoscopic navigation into a gastro-intestinal tract.

2. The locomotion device according to claim 1, wherein the contrast element is a torsion spring.

3. The locomotion device according to claim 1, wherein each of the belts is tensioned by one or more respective pulleys, wherein at least one pulley is movable in a manner allowing a variation of a relative distance between the facing portions.

4. The locomotion device according to claim 3, wherein at least one of the pulleys is mounted onto an oscillating equalizer element.

5. The locomotion device according to claim 1, further comprising a motor configured to drive the pincher and a transmission, the transmission being interposed between the pincher and the motor.

6. The locomotion device according to claim 5, wherein the transmission comprises a reduction unit.

7. The locomotion device according to claim 5, wherein the transmission comprises a coupling between a ring gear and an endless screw.

8. The locomotion device according to claim 1, further comprising an additional pair of rotating elements, the additional pair of rotating elements being drivable in an independent manner to enable a rotation of the locomotion device with respect to the substratum.

9. The locomotion device according to claim 1, comprising an actuator of the pincher, the actuator being capable of enabling a selective driving of the pincher to alternate substratum pinching and moving of the locomotion device with respect to the substratum.

10. An endoscopic capsule comprising one or more locomotion devices according to claim 1.

11. The endoscopic capsule according to claim 10, comprising a plurality of the locomotion devices, each locomotion device of the plurality of locomotion devices being arranged at a respective side of the capsule.

12. The locomotion device according to claim 1, wherein each belt of said pair is provided with a substantially rectilinear portion which remains substantially parallel to, and in contact with, the substratum during operation, each of said rectilinear portions being configured to exercise on the substratum a drawing action caused by friction.

* * * * *